United States Patent [19]

Hsu

[11] Patent Number: 5,922,283

[45] Date of Patent: Jul. 13, 1999

[54] TEST STRIPS FOR THE DETERMINATION OF THE IONIC STRENGTH OR SPECIFIC GRAVITY OF AN AQUEOUS SAMPLE

[75] Inventor: Vincent Hsu, Placentia, Calif.

[73] Assignee: Teco Diagnostics, Anaheim, Calif.

[21] Appl. No.: 08/888,665

[22] Filed: Jul. 7, 1997

[51] Int. Cl.[6] .................................................. G01N 33/48
[52] U.S. Cl. ................... 422/56; 422/61; 436/169
[58] Field of Search ................... 422/56, 58, 61; 436/2, 169

[56] References Cited

U.S. PATENT DOCUMENTS

| | | |
|---|---|---|
| 3,802,842 | 4/1974 | Lange et al. . |
| 3,880,590 | 4/1975 | Ogawa et al. . |
| 4,015,462 | 4/1977 | Greyson et al. . |
| 4,108,727 | 8/1978 | Stiso et al. . |
| 4,318,709 | 3/1982 | Falb et al. . |
| 4,376,827 | 3/1983 | Stiso et al. . |
| 4,532,216 | 7/1985 | Wang . |
| 5,055,407 | 10/1991 | Lau et al. ..................................... 436/2 |
| 5,064,615 | 11/1991 | Mangold et al. . |
| 5,087,575 | 2/1992 | Lau . |
| 5,302,531 | 4/1994 | Bauer ......................................... 436/74 |
| 5,403,744 | 4/1995 | Zimmerle ................................... 436/74 |
| 5,498,528 | 3/1996 | King ........................................... 436/63 |

FOREIGN PATENT DOCUMENTS 0 023 631   2/1981   European Pat. Off. .

*Primary Examiner*—Lyle A. Alexander
*Attorney, Agent, or Firm*—Gregory Garmong

[57] ABSTRACT

The ionic strength or the specific gravity of an aqueous test sample is determined by mixing the sample with a reagent composition on the test strips. The strips comprise a bibulous carrier containing an organic phosphonic acid, such as 1-hydroxyethlidene-1,1-diphosphonic acid and aminotris (methylenephosphonic acid), or inorganic phosphate having one of the structure formulas,

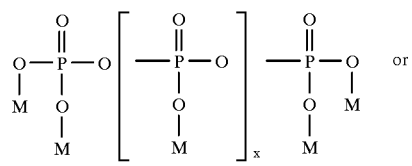

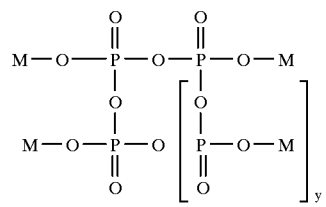

where M stands for one equivalent of an alkali metal, ammonium, lower alkyl ammonium, or hydrogen ion, with the proviso that at least one of the M is hydrogen; x is an integer ranging from zero to two and y is also an integer ranging from zero to one, and serving to buffer the metal ions, and a chromogenic indicator capable of providing a detectable response of the ions being sequestered and coordinated within the complex in the mixture.

16 Claims, No Drawings

TEST STRIPS FOR THE DETERMINATION OF THE IONIC STRENGTH OR SPECIFIC GRAVITY OF AN AQUEOUS SAMPLE

FIELD OF THE INVENTION

The present invention relates to a test strip for the determination of the ionic strength or specific gravity of an aqueous sample, especially of urine. The invention provides an easy way of analyzing the ionic strength or specific gravity whereby test results can be evaluated momentarily by observing the color formation and change in the test area on the strip after simply dipping it to the test solution. The evaluation can also be carried out with the aid of appropriate apparatus.

BACKGROUND OF THE INVENTION AND THE PRIOR ART

Specific gravity, in the case of an aqueous condition, is the ratio of the weight of any volume of the solution to the weight of an equal volume of water taken as the standard, the measurement being made at the same temperature or, as is sometimes the case, at a stated reference temperature. Accordingly, the specific gravity denotes the ratio of the density of the solution with respect to water for the aqueous environment.

There are many important applications in different industrial fields which require the determination of the specific gravity in a liquid such as water softening and deionization, paper and pulp, tanneries, brewing, food processing, mining, agriculture, etc. Although the present invention can be led to a broad range of disciplines, for simplicity this invention is limited to the course of determination of the specific gravity of urine, which is a function of several parameters including the number, valence force, and weight of each dissolved solute in the sample.

Prior to the present invention, numerous physical methods have been utilized in making efforts to directly measure the specific gravity of urine. Some of the most reliable ways include the use of hydrometers, urinometers, pycnometers, dilatometers, gravimeters, and refractometers. However, most of these instruments need cumbersome procedures and calibration before actually being applied to the measurement of specific gravity in the aqueous environment.

An alternative method and device to indirectly determine the specific gravity by measuring the osmolality of urine was disclosed in U.S. Pat. No. 4,015,462. The method utilizes a test strip incorporated with osmotically permeable microcapsules, which contain a solute and a coloring substance. When the strip is brought into contact with the test solution having a lower osmolality or specific gravity than that of the solute inside the microcapsules, the increase of the hydrostatic pressure in the capsules leads to its rupture and releasing of colored dye contents. The intensity of the color formed is proportional to the specific gravity of the test solution. However, the accuracy of specific gravity measured by the osmolality approach could be affected by non-ionic species which are abundantly constituted in the sample solution. Another method, described in U.S. Pat. No. 4,108,727, which utilizes an ionizing agent capable of converting the non-ionic solute to ionizing species of the test solution, is an improvement to eliminate the potential source of inaccuracy caused by the nonionic species in the test sample. However, the microcapsule method on the test strips is difficult to perform for production purpose.

A further method of estimating the specific gravity or the ionic strength without measuring it directly is discussed in U.S. Pat. No. 4,318,709. The test sample is mixed with a reagent composition comprising weakly acidic or basic polyelectrolyte polymers which have been partially neutralized to an extent of at least 50% with a base (such as sodium hydroxide) or an acid (such as hydrochloric acid), and a pH-sensitive compound. The ionic strength of the solution can be determined by the degree of intramolecular pH alteration in the polymer and the deepness of the color being developed by a pH indicator as there exists ion exchange between the polyelectrolyte polymer and the test sample. The specific gravity, therefore, can be subsequently decided by the principle of proportionality between the specific gravity and the ionic strength of an aqueous environment.

Similarly, U.S. Pat. No. 4,532,216 discloses another method which comprises a weakly acidic polyelctrolyte polymer, in which at least 50 percent of the carboxyl groups of which are present in the form of a quaternary ammonium salt, and a pH indicator.

Polyelectrolyte polymers are designated as long-chained (sometimes branched) organic polymers with a multiplicity of ionizable functional groups. When they are placed in water, the type of charge and degree of ionization of these functional groups will determine the charge character of the polyelectrolyte polymer. The weak polyanionic and weak polycationic polymers, as well as the strong polyanionic and strong polycationic polymers are polyacrylic acid and poly (vinylamine), and poly(vinylsulfuric acid) and poly (vinylbenzylammonium chloride) respectively, being mentioned by way of examples.

U.S. Pat. No. 4,376,827 and European Pat. Application No. 023,631 describe a reagent composition for determining the ionic strength or specific gravity of an aqueous test sample. Besides a strongly acidic or strongly basic polyelectrolyte polymer, it contains a buffer substance capable of providing a pH of at least 5.5 and 6.5, respectively, for each patent, as well as a pH indicator.

The disadvantage of using polyelectrolyte polymers in a reagent composition is that the light scattering which is characteristic of solutions of polyelectrolyte macromolecules may become sufficiently pronounced by lowering the charge density on the polymer after simple electrolytes specifically bind to the macroions in the test solution. Thus, the color being developed by the pH chromogenic compound in response to changes in the pH of an aqueous system may shift along the course of time. The result of this slight color change can lead to erroneous interpretations of the specific gravity or ionic strength being measured visually or by the instrument on the test strips.

U.S. Pat. No. 5,064,615 discloses a reagent composition which does not contain any polyelectrolyte polymer for measuring the ionic strength or the specific gravity of aqueous liquids. Besides a pH indicator, the test reagent comprises at least one pH buffer substance, or at least one pH buffer substance and/or at least one complex former. The said complex formers include crown ethers, cryptands, podants and multidentate ligands which contain weakly acidic or weakly basic functional groups.

The properties of the metal ions in the urine and the multidentate ligands in the reagent composition determine the extent of complex formation. The electrostatic forces between small ions of high charge and the said ligands are particularly strong and lead to stable complex formers. However, the univalent large alkali metal ions in the urine such as potassium and rubidium mostly exist as hydrated ions and probably do not form other complex formers; the smaller ions such as lithium and sodium form some weak unstable complexes with some multidentate agents of high charge such as ethylenediamine-tetraacetic acid and bis-(aminoethyl)-glycol-ether-N,N,N',N'-tetraacetic acid. Therefore, if the salts of patients' urine are composed of mainly univalent small and large alkali metal ions, the urine test kits composed of said reagent might not get an accurate result of the specific gravity or ionic strength being measured in the test sample.

Consequently, there is a need for a method to estimate the ionic strength or the specific gravity of an aqueous environment where most of the metals can be stably complexed, and whose method provides the desired test results in which the color developed by the pH chromogen is maintained constantly during the test for a comparatively long period of time.

The present invention departs from the prior state of the art for determining the urine ionic strength or specific gravity in providing a sound improvement of the reagent composition being adopted.

OBJECTS OF THE INVENTION

It is our objective of the present invention to offer a test method which can be carried out efficiently and reliably on a test carrier in order to determine the ionic strength or specific gravity of urine.

SUMMARY OF THE INVENTION

The present invention relates to the determination of the ionic strength or the specific gravity of a test sample. A reagent composition for test strips and test method are disclosed for making this determination in an aqueous test sample. The test reagent comprises an inorganic phosphate or organic phosphonic acid, whose pH has been adjusted to above its metal buffering and ion complexing capacity, and a water soluble pH chromogenic indicator. The test method of the present invention consists of mixing the test sample with one ingredient on the test strips containing said inorganic phosphate or organic phosphonic acid, observing a detectable color response developed by the pH indicator, whose pH value has been adjusted at its pH and metal buffering capacity in the test solution.

DESCRIPTION OF THE INVENTION

The presently claimed test composition contains, a specified ingredient, an inorganic or organic phosphorous compound. The organic phosphorous compounds within the scope of the invention, are those which are hydrolytically stable and can control and buffer metal ion concentration by forming efficient chelating action. Such substances include, for example, aminotris(methylenephosphonic acid) and 1-hydroxyethylidene-1,1-diphosphonic acid. The inorganic phosphates, within the scope of the invention, are those which are stable to any extent in aqueous solution, and those containing more than one $PO_4$ tetrahedra, of which one to three corners are shared with other $PO_4$ tetrahedra, through an oxygen atom common to just one pair of tetrahedra so as to produce P—O—P bonds. They include the unbranched linear phosphates exhibiting the generic formula $M_{x+4}P_{x+2}O_{3x+7}$

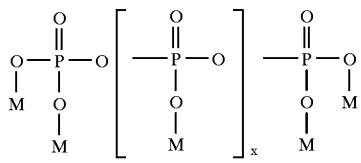

and the cyclic phosphates having the element formula, $M_{y+3}P_{y+3}O_{3y+9}$

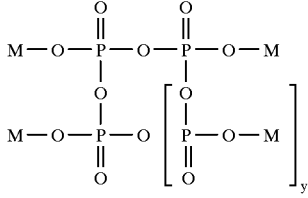

in which M is the chemical equivalent of an alkali metal, an ammonium, a lower alkyl ammonium, or a hydrogen ion, and x is any whole number ranging from 0 to 2 and y is a whole number either 0 or 1.

Numerous examples of such compounds of general formula (I) and (II) are known in the art, their common characteristics residing in the formation of relatively strongly soluble complexes with the alkali and alkaline earth metals as well as with transition metals. Some of the compounds of general formula (I) and (II) are viscous liquids at ambient temperature, whereas some of them are sparsely soluble in water, and become multiply charged negative species. The readily water-soluble compounds of general formula (I) and (II) are most suitable for the presently claimed art. Preferred compounds of the formula (I) and (II) are exemplified as follows with the meaning of the symbols to the respective general formula:

hexaammonium tetrapolyphosphate (formula I: M is an ammonium, and x=2); tetrasodium pyrophosphate decahydrate (formula I: M is a sodium, and x=0); tetramethylammonium tripolyphosphate (formula I: M is a tetramethylammonium, and x=0); sodium tripolyphosphate (formula I: M is a sodium, and x=0); pentapotassium tripolyphosphate (formula I: M is a potassium, and x=0); tripolyphosphoric acid (formula I: M is a hydrogen, and x=0); and compounds of the metaphosphates, for example trimetaphosphoric acid (formula II: M is a hydrogen, and y=0) and tetraammonium tetrametaphosphate (formula II: M is an ammonium, and y=1).

The composition of the present invention includes the said inorganic phosphates or organic phosphonic acids, whose pH values have been suitably titrated by an acid or base to reflect their metal complexing and pH buffering capacity. The inorganic phosphate salts, thus, consist of at least one ionizable hydrogen atom. This hydrogen ion bound to the oxygen atom of the $PO_4$ tetrahedra dissociates upon complex formation between the inorganic phosphate salts and the metals in the aqueous solution under appropriate pH condition. All polyphosphoric acids and their salts have the common pH titration curves where inflection points are near pH 4.5 and 9. At these pH ranges, the currently said phosphates are to be partially titrated with either an acid or base to release at least one proton upon complexing with the metals. The amount of protons which are to be released is correlated with the ionic strength or specific gravity of the test solution.

To a first approximation, the partially HCl titrated tetrasodium pyrophosphate employed to buffer and complex $Ca^{+2}$ ions in equilibria may be exemplified as follows:

pH < 3

$NoCa^{+2}$ – pyrophosphate complex formation

4 < pH < 6

$$Ca^{+2} + H_2P_2O_7^{2-} \rightleftarrows CaP_2O_7^{2-} + 2H^+$$

$$K_{eq} = \frac{[CaP_2O_7^{2-}][H^+]^2}{[Ca^{+2}][H_2P_2O_7^{2-}]} = 10^{-2}$$

7 < pH < 9

$$Ca^{+2} + HP_2O_7^{3-} \rightleftarrows CaP_2O_7^{2-} + H^+$$

$$K_{eq} = \frac{[CaP_2O_7^{2-}][H^+]}{[Ca^{+2}][HP_2O_7^{2-}]} = 10^4$$

As pH > 10

$$Ca^{+2} + P_2O_7^{4-} \rightleftarrows CaP_2O_7^{2-}$$

$$K_{eq} = \frac{[CaP_2O_7^{2-}]}{[Ca^{+2}][P_2O_7^{4-}]} = 10^{13}$$

The above illustration depicts the relationship of the equilibrium concentration between pyrophosphate and $Ca^{+2}$-pyrophosphate complex $(CaP_2O_7^{2-})$ under various pH environments. The preferred pH titration range is 7<pH<9, where $K_{eq}$ is the optimum for proton release.

Based on the values of $K_{eq}$ a number of said phosphates can be selected to exhibit the same result at the preferred pH condition. For a complete list of equilibrium constants for such metal complexes, it is referred to the tables of data published by the Chemical Society under the supervision of International Union of Pure and Applied Chemistry (Stability constants, Part II, Inorganic Ligands, No. 6, The Chemical Society, London, 1968 ).

The preferred pH ranges for the test sample, accordingly, will be between 4 to 10 for all polyphosphates. pH values beyond the range can be adjusted to the territory by adding acid or base before or during the measurement of the ionic strength. The method of present invention is well suited for urine specific gravity investigation since the pH values of urine usually lie in the range of 5 to 8.5. The values of specific gravity being determined by using this method lie between 1.002 to 1.10. These values are also within the territory of the specific gravity of human urine.

In the event that the reagent composition is applied to an absorbent carrier matrix the pH value of the impregnation solution is, at first, carefully adjusted to a pH value of 5 to 9, preferably of 6.5 to 8.5, whose pH value is dependent upon the ionic strength or the specific gravity of the test liquid.

The concentration of said inorganic phosphate or organic phosphorus compounds in the reagent composition according to the present invention totals $2.5 \times 10^{-3}$ g/ml to $5 \times 10^{-2}$ g/ml and preferably in the amount of $4 \times 10^{-3}$ g/ml to $3.5 \times 10^{-2}$ g/ml.

In addition, a pH chromogenic indicator is included in the reagent composition for detecting a relatively small change in pH in the range of the metal buffering capacity of the polyphosphates. The use of color changes to measure pH values rests upon (1) the existence of indicator substances the colors of which are dependent upon pH, and (2) the ability of those substances to produce recognizable colors at such low concentrations that the pH of the medium is not significantly altered by their presence. The pH indicators may be considered to be weak acids and bases. The measurement of color reveals the ratio of the concentrations of the conjugate acid and base forms of the indicator which in turn is indicative of the ionic strength or specific gravity of the aqueous system being tested. The pH measurements may be derived by Debye-Hückel equation with known ionic strengths if the dissociation constant of the indicator is known.

In the most common procedure for pH measurements with the chromogenic indicators, the color of the test solution with added indicator is matched with color standards prepared from a series of buffer solutions of known pH containing the same concentration of indicator as does the test solution. The alteration of the amount of salt to a solution produces a real change in the pH and the ionic strength or specific gravity being measured as well as an apparent change indicated by the color tone of the chromogens. The choice of an indicator to be used in the present invention are those whose color-change intervals include the pH which was adjusted in the test liquid. For the determination of the ionic strength or of the specific gravity of urine, pH chromogens with transition interval of 5 to 10 are most favorable. Any pH indicator undergoing color change within this range of pH values gives satisfactory results for the determination of urine ionic strength or specific gravity. Examples of such pH chromogens are dichlorophenolsulfonphthalein, dimethyldiaminophenazine chloride, dibromothymolsulfonphthalein, phenolsulfonphthalein, and thymolsulfonphthalein. Of these, dibromothymolsulfonphthalein and thymolsulfonphthalein are found to be especially suitable due to their desirable colors produced upon contacting with urine.

To use an indicator, the reagent solution is prepared to contain 0.05–0.2% (w/v) of the pH indicator. Water is generally used as the solvent, but an alcohol—water mixture is used if the indicator is not sufficiently soluble in water. If an alcohol—water mixture is used, the pH indicator is first dissolved in alcohol, then diluted with water and alcohol to make the indicator concentration 0.05–0.2% and the alcohol concentration 50–80%. Among the choices of indicators, dimethyldiaminophenazine chloride is usually made up in alcohol—water solution whereas the others are readily soluble in water.

The desirable embodiment of the present invention is to apply the reagent composition, as a coating layer, unto an absorbent carrier described in U.S. Pat. No. 3,802,842 to provide a rapid and reliable examination of the specific gravities of aqueous solution. Suitable absorbent carriers are filter papers, fleeces made of fibers or plastics, or polyester fleeces. Other materials which can absorb the impregnation solution may alternatively be utilized. The absorbent carriers are impregnated with the test reagent in a manner that the bibulous material of the carriers is fully saturated by the impregnation solution with which it is contacted. In general, submission of the bibulous material in the reagent solution for about 5 minutes is sufficient for the purpose of impregnation. The impregnated carriers are then dried under appropriate temperature whereby a film of impregnated solution is formed on the entire surface. The dried carriers either can be cut into handy strips, or they can be processed into square pieces which can be glued or sealed onto plastic films or metallic strips. Additional ancillary materials might also be included in the reagent composition, such as wetting agents and/or stabilizers.

For the preparation of the test strips according to the present invention for investigation of urine specific gravity, the test area of the test strip is consisted of an absorbent carrier such as filter paper or fleece of synthetic fibers which has been impregnated with the test reagent, and then dried. The test reagent contains a mixture of a water soluble inorganic phosphate or organic polyphosphonic acid, for example, sodium tripolyphosphate or 1-hydroxyethylidene-1,1-diphosphonic acid, respectively, whose pH value has been adjusted to its metal complexing and buffering capacity at pH=7.5; and a pH chromogenic indicator, for example, dibromothymolsulfonphthalein. The test area of the test strip is brought into contact with the urine sample by dipping the test strip into the aqueous sample, and the test strip can be taken out of the sample as long as the test area on the test strip becomes wet. Any color response on the test area of the test strip is then compared with the color scale of a reference standard associated with the values of the specific gravity to be determined. The reference specific gravity color scale, with the aid of a pH indicator, can be obtained by comparing the recorded colors of a series of comparable solutions of known ionic strength or specific gravity.

The following examples are set forth for purposes of illustration only and are not to be construed as limitations on the present invention except as set forth in the appended claims.

EXAMPLE 1

A filter paper No. 903 of the firm Schleicher and Schüll is impregnated with an aqueous solution of the following compositions:

trimetaphosphoric acid: 1.2 g
dibromothymolsulfonphthalein: 0.18 g
distilled water: 100 ml
adjust to pH=7.5 with 3N sodium hydroxide solution The impregnated filter paper is dried in a drying oven at 55° C., and then cut into small squares the size about 6×6 mm. The so produced test area is laminated onto a plastic strip of 6×60 mm.

Upon immersion of the test strip into the urine sample, the color response on the test area of the test strip can be compared with the color scale which has been recorded and prepared from a series of aqueous solution of known ionic strength, subsequently determining the specific gravity of the urine sample. The color transition of the test area summarized in TABLE I upon contact and interaction with standard solution are sufficiently differentiable to provide a method of measuring test sample specific gravity.

TABLE I

COLOR TRANSITION OF A REAGENT COMPOSITION INCLUDING DIBROMOTHYMOLSULFONPHTHALEIN AND TRIMETAPHOSPHORIC ACID UPON CONTACT WITH STANDARDIZED SOLUTIONS (pH = 7.5)

| Specific Gravity of Standardized Solution | Ionic Strength (molar) | Observed Color |
|---|---|---|
| 1.000 | 0 | Sky Blue |
| 1.005 | 0.125 | Blue-Green |
| 1.015 | 0.50 | Green |
| 1.025 | 1.00 | Mustard-Yellow |
| 1.030 | 1.36 | Yellow |

EXAMPLE 2

A filter paper No. 903 of the type Schleicher & Schüll is treated with the impregnation solution of the following compositions:

1-hydroxyethylidene-1,1-diphosphonic acid: 0.7 g
thymolsulfonphthalein: 0.12 g
distilled water: 100 ml
adjust to pH=7.5 with 2N tetramethylammonium hydroxide solution The impregnated filter paper is subsequently dried in a drying cabinet at 55° C. until it has a residual moisture of less than 3 %, and then cut into a piece the size of 6×6 mm. The so produced test area is glued or stuck onto a plastic strip of 6×60 mm.

The test strip produced is dipped into the standardized urine solutions having a specific gravity of 1.000 to 1.030. The color responses produced after 10 seconds, 60 seconds, 120 seconds, 240 seconds, and 360 seconds were illustrated in TABLE II:

TABLE II

| Specific gravity of standardized solution | Color Response | | | | |
|---|---|---|---|---|---|
| | 10 seconds | 60 seconds | 120 seconds | 240 seconds | 360 seconds |
| 1.000 | blue | dull blue | dull blue | dull blue | dull blue |
| 1.010 | blue-green | blue-green | blue-green | blue-green | pea-green |
| 1.020 | light green | light green | light green | light green | light green |
| 1.030 | yellow-brown | yellow-brown | yellow-brown | buff | buff |

Furthermore, it is found surprisingly that the colors developed in the test area of the test strips are still remaining constant even after the strips have been taken out from the urine sample for 6 minutes.

EXAMPLE 3

A filter paper No. 903 of the firm Schleicher & Schüll is impregnated with a solution of the following components:

pentapotassium tripolyphosphate: 0.85 g dibromothymolsulfonphthalein: 0.1 g distilled water: 100 ml pH of the solution is adjusted to 7.6 with 0.5M tripolyphosphoric acid The impregnated filter paper is dried and then cut into pieces of small squares the size of 6×6 mm. The so produced test area is stuck onto a plastic strip of 6×60 mm.

EXAMPLE 4

A filter paper No. 903 of the firm Schleicher & Schüll is impregnated with a solution of the following components:

Hexaammonium tetrapolyphosphate: 1.2 g dibromothymolsulfonphthalein: 0.1 g distilled water: 100 ml The pH value of the solution is adjusted to 7.6 with 2N hydrochloric acid The impregnated yellowish-green filter paper is dried for about 10 minutes at 55° C. in a drying cabinet, and then cut into a piece the size of 6×6 mm. The bibulous test area is laminated onto a plastic strip of 6×60 mm.

The test strips produced from Example 3 and 4 are dipped into an urine sample. The colors of the test area are also remaining constant for more than 5 minutes as illustrated in TABLE II after mixing the strips with the urine sample and then withdrawn from the urine. The values of specific gravity measured in the urine sample obtained from Example 3 and 4 are in agreement with the ones of the same urine sample determined by the use of a refractometer. agreement with the ones of the same urine sample determined by the use of a refractometer.

The preceding examples can be repeated with similar success when, instead of the foregoing phosphorous compounds illustrated in the examples, the following substitutes are employed, such as tetrasodium pyrophosphate, sodium tripolyphosphate, tetramethylammonium tripolyphosphate, pyrophosphoric acid, or (α-aminomethyl) polyphosphonic acids.

From the foregoing description, it will be understood that the specification and examples are illustrative but not limitative of the present invention inasmuch as other embodiments within the spirit and scope of the invention will be easily ascertained to the essential characteristics of the skills in the art.

What is claimed is:

1. A test strip capable of determining the ionic strength or specific gravity of an aqueous test sample containing cations, said strip comprising a porous absorbent carrier matrix impregnated with a test reagent comprising a pH chromogenic indicator selected from the group consisting of dibromothymolsulfonphthalein and thymolsulfonphthalein, and a reagent selected from the group consisting of 1-hydroxyethlidene-1,1-diphosphonic acid, aminotris(methylenephosphonic acid), a first inorganic phosphate having a structural formula

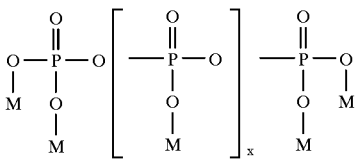

the first inorganic phosphate having been titrated by an acid or base to achieve its metal complexing and buffering capacity, and wherein M stands for one equivalent of an alkali metal, ammonium, lower alkyl ammonium, or hydrogen ion, and x is an integer ranging from zero to two, and a second inorganic phosphate having a structural formula,

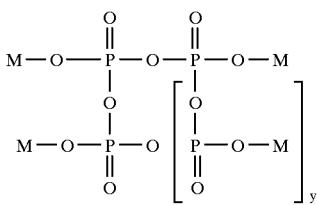

the second inorganic phosphate having been titrated by an acid or base to achieve its metal complexing and buffering capacity, and wherein M stands for one equivalent of an alkali metal, ammonium, lower alkyl ammonium, or hydrogen ion, and y is an integer ranging from zero to one.

2. The test strip of claim 1, wherein the pH of the reagent is in the range of pH 5 to 9.

3. The test strip of claim 1, where in the pH of the reagent is in the range of pH 6.5 to 8.5.

4. The test strip of claim 1, wherein the reagent is the first inorganic phosphate and is selected from the group consisting of hexaammonium, tetrapolyphosphate, sodium tripolyphosphate, tetramethylammonium tripolyphosphate, and tetrasodium pyrophosphate decahydrate.

5. The test strip of claim 1, wherein the reagent is the second inorganic phosphate and is selected from the group consisting trimetaphosphoric acid, and tetraammonium tetrametaphosphate.

6. The test strip of claim 1, wherein the reagent is 1-hydroxyethlidene-1,1-diphosphonic acid, whose pH is adjusted to 7.5, and the pH chromogenic indicator is dibromothymolsulfonphthalein.

7. A test strip capable of determining the ionic strength or specific gravity of an aqueous test sample containing cations, said strip comprising a porous absorbent carrier matrix impregnated with a test composition comprising a pH chromogenic indicator, and a reagent buffered in the range of pH 5 to 9, the reagent being selected from the group consisting of an organic phosphonic acid, a first inorganic phosphate having a structural formula

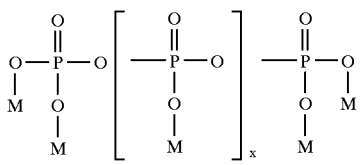

wherein M stands for one equivalent of an alkali metal, ammonium, lower alkyl ammonium, or hydrogen ion, and x is an integer ranging from zero to two, and a second inorganic phosphate having a structural formula,

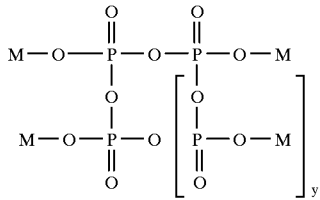

wherein M stands for one equivalent of an alkali metal, ammonium, lower alkyl ammonium, or hydrogen ion, and y is an integer ranging from zero to one.

8. The test strip of claim 7, where in the pH of the reagent is in the range of pH 6.5 to 8.5.

9. The test strip of claim 7, wherein the reagent is the first inorganic phosphate and is selected from the group consisting of hexaammonium tetrapolyphosphate, sodium tripolyphosphate, tetramethylammonium tripolyphosphate, and tetrasodium pyrophosphate decahydrate.

10. The test strip of claim 7, wherein the reagent is the second inorganic phosphate and is selected from the group consisting trimetaphosphoric acid, and tetraammonium tetrametaphosphate.

11. The test strip of claim 7, wherein the reagent is hexaammonium tetrapolyphosphate.

12. The test strip of claim 7, wherein the pH chromogenic indicator is dibromothymolsulfonphthalein.

13. The test strip of claim 7, wherein the reagent is hexaammonium tetrapolyphosphate and the pH chromogenic indicator is dibromothymolsulfonphthalein.

14. The test strip of claim 7, wherein the reagent is tetramethylammonium tripolyphosphate.

15. The test strip of claim 7, wherein the reagent is tetrasodium pyrophosphate decahydrate.

16. The test strip of claim 7, wherein the reagent is 1-hydroxyethlidene-1,1-diphosphonic acid.

* * * * *